United States Patent [19]

Zupančič et al.

[11] 4,147,729
[45] Apr. 3, 1979

[54] 1-(3-BENZOYLPHENYL)-PROPINE AND PROCESS FOR THE PREPARATION THEREOF

[75] Inventors: Boris Zupančič, Ljubljana; Branko Jenko, Ljubljana-Polje, both of Yugoslavia

[73] Assignee: LEK tovarna farmacevtskih ibn kemicnih izdelkov, n.sol.o, Ljubljana, Yugoslavia

[21] Appl. No.: 842,821

[22] Filed: Apr. 3, 1979

[30] Foreign Application Priority Data

Oct. 18, 1976 [YU] Yugoslavia .......................... 2547/76
Oct. 18, 1976 [YU] Yugoslavia .......................... 2549/76

[51] Int. Cl.² ............................................. C07C 49/76
[52] U.S. Cl. ..................................... 260/591; 562/460
[58] Field of Search ........................... 260/591, 671 A

[56] References Cited

U.S. PATENT DOCUMENTS 3,751,446   8/1973   Heck ................... 260/671 A

OTHER PUBLICATIONS

Castro et al., J. Org. Chem., vol. 31, pp. 4071–4078 (1966).
Stephens et al., J. Org. Chem., vol. 28, pp. 3313–3315 (1963).
Castro et al., J.A.C.S., vol. 91, pp. 6464–6469 (1969).
Bohlmann et al., Chem. Ber., vol. 108, pp. 2149–2151 (1975).

Primary Examiner—James O. Thomas, Jr.
Assistant Examiner—James H. Reamer
Attorney, Agent, or Firm—Pollock, Vande Sande & Priddy

[57] ABSTRACT 1-(3-Benzoylphenyl)-propine represented by the formula:

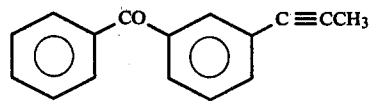

useful as an intermediate is provided.

1 Claim, No Drawings

1-(3-BENZOYLPHENYL)-PROPINE AND PROCESS FOR THE PREPARATION THEREOF

The present invention relates to the novel compound 1-(3-benzoylphenyl)-propine and to a process for the preparation thereof.

This novel compound is an intermediate for the manufacture of 2-(3-benzoylphenyl)-propionic acid, which is characterized by an optimum analgo-antirheumatical activity.

A process for preparing 2-(3-benzoylphenyl)-propionic acid from 1-(3-benzoylphenyl)-propine is described in our Yugoslavian Pat. application P 2547/76, filed on Oct. 18, 1976.

The inventive process is disclosed by the following schemes 1 and 2.

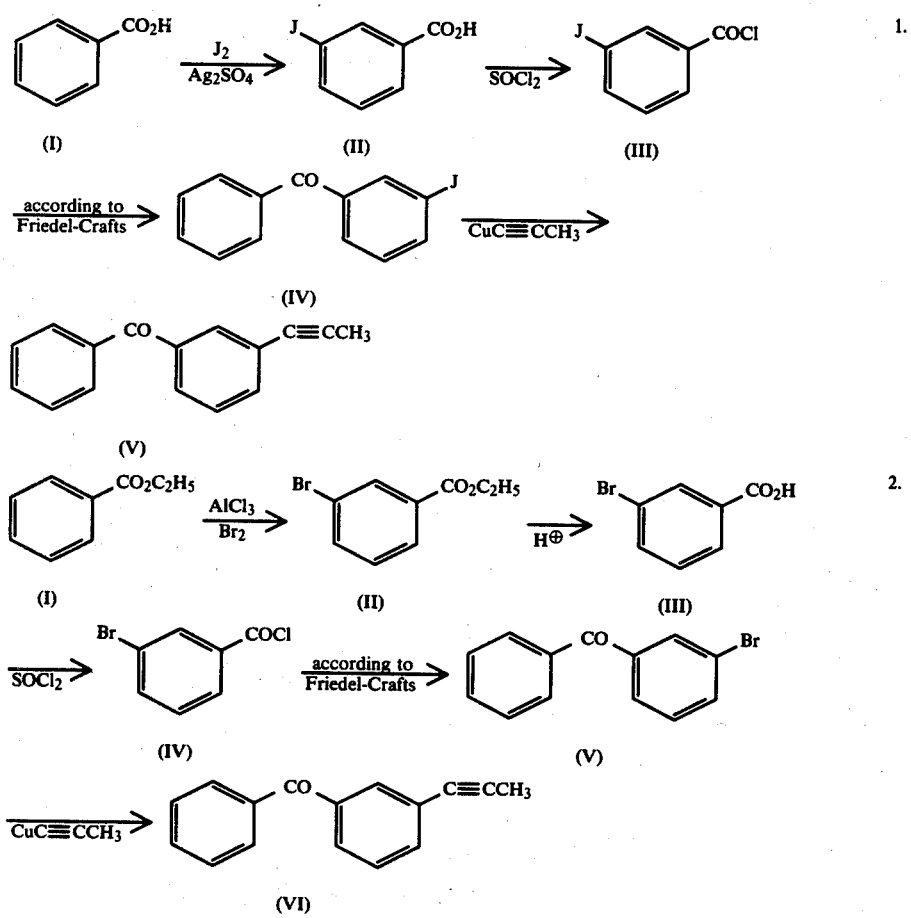

According to scheme 1 the starting substance is benzoic acid, whereas according to scheme 2 the starting substance is the ethylester thereof. Both starting substances are low-priced and easily available on the market.

The essential feature of the process is the reaction of 3-halo-benzophenone, wherein "halo" stands for bromo or iodo, with Cu-propine.

The working temperature is 160° to 240° C. and the pressure is 5 to 15 atm. Pyridine is the preferred reaction medium.

The present invention is illustrated by the following Examples.

EXAMPLE 1

An autoclave of 200 ml., equipped with a heater and stirrer, is charged with 26.6 g. of 3-iodo-benzophenone, m.p. 38.5° to 42.5° C., lit. 44°. (B. V. Trunov, E. S. Novikova, zur. obšč. himii 26, 1994 (1956)), 8.9 g. of Cu-propine (W. R. Pilgrim's Ph.D. Thesis, p. 47, Queen's University, Kingston, Ontario, Canada, March 1969), and 80 ml. of pyridine, whereupon it is evacuated seven times and charged with nitrogen. Finally the autoclave with the nitrogen atmosphere is closed.

Under stirring the reaction mixture is heated to 110° to 120° C. and after 17 hours it is cooled down to ambient temperature and poured into 500 ml. of water. The precipitated CuI is filtered off and washed with 200 ml. of ether. In a separating funnel the aqueous layer is separated and extracted with two 150 ml. portions of ether. The combined ether extracts are washed with two 75 ml. portions of 5% w./w. HCl and then with four 75 ml. portions of water. The product is dried over $Na_2SO_4$, filtered and transferred into a distillation apparatus. The main fraction distills over at 185° to 196° C./0.4 mm. Hg.

Yield: 16.0 g. (84.3% theor.), gas chromatography 97%.

Analysis: $C_{16}H_{12}O = 220.10$: Calculated: C, 87.30; H, 5.46. Found: C, 86.86; H, 5.38.

IR:
$\nu/C\equiv/=2240$ cm$^{-1}$
$\nu/CO/=1670$ cm$^{-1}$
n m r:
$\delta/-CH_3/:240/s/$ δ/9H/:7.96/m/

EXAMPLE 2

An autoclave of 200 ml. is successively charged with 26.6 g. of 3-bromobenzophenone, 10.3 g. of Cu-propine and 80 ml. of pyridine (dried over NaOH), evacuated seven times and charged with nitrogen. Finally, the autoclave with the nitrogen atmosphere is closed and heated under stirring to 230° C., whereby the pressure increases to about 15 atm. After 48 hours of stirring at the cited temperature, the reaction mixture is cooled down and poured into 500 ml. of water. The precipitated CuBr is filtered off and washed with 200 ml. of ether. The aqueous layer is extracted with two 150 ml. portions of ether, and the combined ether extracts are washed with two 150 ml. portions of 5% w./w. HCl. After washing with three 150 ml. portions of water, the product is dried over $Na_2SO_4$.

$Na_2SO_4$ is filtered off and the ether is evaporated in a rotation evaporator, whereupon the residual oil is distilled over at 185° to 196° C/0.4 mm. Hg.

Yield: 18.0 g. (80.2% theor.).

Analysis: thin-layer chromatography: 1 spot (chloroform, silica gel 60 $F_{254}$).

What is claimed is:

1. The compound 1-(3-benzoylphenyl)-propine.

* * * * *